United States Patent
Eisemann et al.

[19]

[11] Patent Number: 5,920,400
[45] Date of Patent: Jul. 6, 1999

[54] METHOD AND DEVICE FOR DETERMINING THE PURITY AND/OR PRESSURE OF GASES FOR ELECTRIC LAMPS

[75] Inventors: Hans Eisemann; Karen Twesten, both of Berlin, Germany

[73] Assignee: Patent-Treuhand-Gesellschaft für elektrische Glühlampen mbH

[21] Appl. No.: 08/860,805

[22] PCT Filed: Feb. 14, 1996

[86] PCT No.: PCT/DE96/00232

§ 371 Date: Jul. 9, 1997

§ 102(e) Date: Jul. 9, 1997

[87] PCT Pub. No.: WO96/25658

PCT Pub. Date: Aug. 22, 1996

[30] Foreign Application Priority Data

Feb. 15, 1995 [DE] Germany .................... 195 05 104

[51] Int. Cl.⁶ ........................................................ G01J 3/46
[52] U.S. Cl. ...................... 356/425; 356/311; 356/313; 356/314
[58] Field of Search .................... 356/425, 311, 356/313, 314

[56] References Cited

U.S. PATENT DOCUMENTS

| | | | |
|---|---|---|---|
| 2,509,649 | 5/1950 | Norman | 356/311 |
| 3,292,988 | 12/1966 | Kimball . | |
| 4,759,630 | 7/1988 | Yuasa et al. . | |
| 4,801,209 | 1/1989 | Wadlow | 356/311 X |
| 5,168,323 | 12/1992 | Purtschert et al. . | |

FOREIGN PATENT DOCUMENTS 0 617 274 A1  9/1994  European Pat. Off. .
2 185 573     7/1987  United Kingdom .

OTHER PUBLICATIONS

"Technisch–wissenschaftliche Abhandlungen der Osram–Gesellschaft" (Technological–Scientific Papers of the Osram Company, vol. 12, published by Osram GmbH, 1986, article by M. Gaugel: Gasreinheitstest bei Halogen–Glühlampen mit Hilfe eines Spektrallinienvergleichs (Gas Purity Test in Halogen Incandescent Lamps with the Aid of Spectral Line Comparison, pp. 546–549.

Primary Examiner—Frank G. Font
Assistant Examiner—Reginald A. Ratliff
Attorney, Agent, or Firm—Frishauf, Holtz, Goodman, Langer & Chick, P.C.

[57] ABSTRACT

According to the method the intensity of at least one pressure-independent (impurity detection) or pressure-dependent (gas pressure determination) spectral line is measured selectively. Indirect detection utilizes the intensity of spectral lines whose wavelengths correspond to higher levels of excitation energy than those of the impurities. The intensity of these spectral lines is a measure of the impurities. Alternatively, the intensity of at least one spectral line of the respective impurity is measured directly. In order to eliminate co-phasal interference, two spectral lines are measured and the ratio is formed therefrom. The intensity ratio of argon lines of wavelengths $\lambda_1=772.4$ nm and $\lambda_2=738.4$ nm has in particular proved acceptable for the indirect detection of impurities in argon and the intensity ratio V of the argon lines of wavelengths $\lambda_1=763.5$ nm and $\lambda_2=738.4$ nm has proved acceptable for determining the argon pressure. The measuring process is in particular suitable for integration in high-speed production lines for discharge lamps.

38 Claims, 3 Drawing Sheets

METHOD AND DEVICE FOR DETERMINING THE PURITY AND/OR PRESSURE OF GASES FOR ELECTRIC LAMPS

FIELD OF THE INVENTION

The invention relates to a method for detecting impurities in gases, especially noble gases, or gas mixtures for electric lamps or radiators and to a method for measuring the pressure of gases, especially noble gases, or the gas components of gas mixtures for electric lamps or radiators. The invention also relates to an apparatus for performing these methods.

The term "electric lamps" includes both incandescent and discharge lamps. The term "electric radiators" is understood to mean gas discharges that emit primarily electromagnetic radiation outside the visible range, especially in the UV or IR range.

The methods utilize the influence of the gas pressure or of impurities on the fluorescence spectrum of a gas discharge, especially a glow discharge.

BACKGROUND

Gaseous or vapor-form as well as solid substances whose presence in gases or gas mixtures for electric lamps or radiators—hereinafter called gas system for brevity—is undesired and are designated as impurities. As a rule, these impurities enter the gas system in an uncontrolled way, for instance even during lamp production by means of contaminated rinsing gases or fill gases or through leaky pumping and filling systems. Even in the finished lamp, however, impurities can enter the gas system of the lamp, for instance through leaks of the lamp bulb itself or even during lamp operation, for instance through contaminated electrodes or increased electrode burnoff from inadequate fill pressure. The consequence of impurities—of whatever source—is in the final analysis nonfunctional lamps, or lamps of limited service life or maintenance.

The goal of all these efforts is therefore to assure the least possible contamination of the gas system even during lamp production. Moreover, for the sake of seamless quality control it is desirable that finished lamps with unacceptably high contamination or excessive deviations from the desired fill pressure be detected and rejected. With this background, rapid, reliable detection of corresponding impurities and monitoring of the fill pressure become quite important.

One method for determining the gas purity is known from the contribution by M. Gaugel entitled "Gasreinheitstest bei Halogen-Glühlampen mit Hilfe eines Spektrallinienvergleichs" [Gas Purity Test in Halogen Incandescent Lamps using Spectral Line Comparison] to the book series entitled "Technisch-Wissenschaftliche Abhandlungen der OSRAM-Gesellschaft" [Technical-Scientific Treatises at OSRAM], Vol. 12, pp. 546–549, Springer-Verlag, Berlin 1986. There, the light of halogen incandescent lamps is split by two beam splitters into three beams of light and delivered to three spectrally differently sensitive photomultipliers. The maximum spectral sensitivity of the individual photomultipliers is located at the wavelength of about 410 nm, 523 nm and 616 nm respectively, that is, in the blue, green and red range of the electromagnetic spectrum. By means of two analog dividers, the ratios of the "red/blue" and "red/green" photomultiplier signals are formed and compared by two comparators to find whether the corresponding values are within preadjustable tolerance range. If not, the halogen incandescent lamp is found to be defective; that is, either a fill error and/or excessive gas contamination has occurred.

A disadvantage of this embodiment is that the halogen incandescent lamp to be tested must, including its optical setup and photomultipliers, be located inside an opaque housing during the measurement. Otherwise, in-phase interference signals, such as ambient light, cause incorrect measurements, since these interference signals are weighted spectrally completely differently by the three photomultipliers and are therefore not eliminated in the quotient formation.

U.S. Pat. 4,759,630 Vuasa et al., discloses an arrangement for determining the quality of incandescent lamps. It includes a device for generating a discharge between the incandescent coil and an electrode mounted on the outer wall of the lamp bulb, and an apparatus for analyzing the radiation emitted by the discharge in the wavelength range between 550 nm and 570 nm. The lamp quality is judged from the behavior over time of this radiation, which is optionally compared with the radiation in the wavelength range between 660 nm and 680 nm.

In U.S. Pat. 3,292,988, the intensity of spectral lines of the fill gas component argon that have wavelengths greater than 650 nm is used to monitor the mercury vapor pressure in fluorescent lamps during lamp operation.

U.S. Pat. 5,168,323 proposes an apparatus and a method for determining impurities in a gas. The apparatus includes two opposed electrodes, between which the gas flows; a low-frequency alternating voltage source connected to the electrodes; and an optimal measuring instrument. With the aid of the alternating voltage source, an arc discharge is generated whose emission lines are detected by means of the measuring instrument. From the intensities of characteristic spectral lines of the various impurities, their concentration is determined with the aid of a linear equation system.

THE INVENTION

A first object of the invention is to overcome the disadvantages discussed and to disclose a relatively simply attainable method, which in particular can be integrated into lamp production, for detecting impurities in gases or gas mixtures for electric lamps or radiators. The method should moreover be suitable in particular for monitoring the function and/or quality of electric lamps.

A further object of the invention is the determination of the pressure of gases, especially noble gases, or the gas components of gas mixtures for electric lamps or radiators. Moreover, the method should be suitable in particular also for monitoring the function and/or quality of electric lamps or radiators.

Still another object of the invention is provide an apparatus with which the proposed methods can be performed.

Briefly, by means of a gas discharge, the gas or gas components of the mixture and the impurities possibly contained therein are excited to emit electromagnetic radiation. Detecting possibly admixed gaseous and/or vapor-form impurities or detecting the pressure of the gas or gas component is effected by means of the measured intensity of one or more suitable spectral lines of this radiation.

In accordance with a feature of the invention, impurities are detected by purposefully using one or more spectral lines whose intensities in the relative pressure range, that is, fill pressures in electric lamps, are largely pressure-independent. In this way, incorrect measurements from pressure fluctuations of the gas are averted. For the practical acceptability of the method this is of major significance, especially for detecting impurities in the lamp vessels of electric lamps, since the fill pressures of the lamps vary as a function of production variations. Spectral lines whose intensities are pressure-dependent can therefore produce false results. If unlike the invention the intensity of the radiation is integrated over a relatively broad wavelength range, then in unfavorable cases pressure-dependent spectral lines can be detected as well. The consequence is incorrect measurements, if the fill pressure fluctuates.

The concrete selection of suitable spectral lines takes into account possibly present gas components, such as the fill components of metal halide high-pressure discharge lamps. Only individual spectral lines that do not overlap or coincide with other lines of the fluorescence spectrum are selected. The permissible spacing of the selected lines from neighboring lines should advantageously be greater than the spectral resolution of the measurement. This prevents the intensity of undesired lines from being measured as well and the attendant adulteration of the result.

In accordance with another feature of the invention for determining the pressure of gases, in particular noble gases, or the gas components of gas mixtures, one or more spectral lines of the gas or applicable gas component is purposefully used; the intensity of at least one so used spectral line is pressure-dependent. In a pressure range dependent on the excitation conditions, typically from the prevacuum range to atmospheric pressure, and in particular in the range between approximately 0.1 kPa and approximately 40 kPa, the intensity of suitable spectral lines increases with the pressure. With the aid of the measured pressure-dependent intensity and a calibration measurement value, the absolute pressure of the gas or the partial pressure of the corresponding gas component is then ascertained.

A very essential aspect of the methods in accordance with the invention is the selective measurement of the spectral lines. It has in fact been found in preliminary experiments that reliable results under production technology conditions can be attained only if the measurement conditions explained hereinafter are adhered to.

In improved variants of both methods, a quotient of the intensities of two spectral lines is formed, with the intensity of at least one line being pressure-independent. Preferably the two spectral lines are so close together that noise signals and in-phase interference signals, especially ambient or scattered light, are assessed spectrally virtually identically. The spacing of the two spectral lines is typically less than about 100 nm and preferably less than about 50 nm. Since the aforementioned interference signals within this spacing have a virtually constant spectral intensity distribution, or in other words are present in relatively broad bands in comparison to the selected spectral lines, they are largely eliminated in the quotient formation. In-phase signal attenuations, for instance caused in electric lamps by bulb blackening, are likewise eliminated. For these reasons, the ratio measurement described (ratiometric measuring method) is to be preferred over a fundamentally possible absolute measurement of the intensity of a single spectral line, in which interference effects greatly adulterate the outcome of measurement, which as a rule cannot be corrected retroactively.

The selection of suitable special lines for the ratio measurement depends on the specific gas or gas components. In the case where argon is present, suitable spectral lines are in the wavelength range between 650 nm and 800 nm, or between 800 nm and 1000 nm.

In a concrete embodiment of the method for detecting impurities, at least one spectral line of the gas or of a gas component whose intensity is independent of fill pressure; is purposefully selected, and whose wavelength or wavelengths correspond to a higher excitation energy than that of the spectral lines of the expected impurities to be determined. Impurities that may possibly be present are consequently excited preferentially. In simplified terms, some of the electric power of the gas discharge enters increasingly into these "loss channels", instead of into the occupation of the excited states, corresponding to the selected spectral lines, of the gas or gas components. As a result, the intensities of the selected spectral lines decrease (the corresponding optical transitions are increasingly "quenched" by the impurities; that is, the density of occupation of the associated excited states decreases), and in fact all the more so, the higher the concentration of the impurities ("quench partners"). For this reason, the attenuation of the intensities of the selected spectral lines is indirect evidence of impurities located inside the lamp vessel.

The advantage of this indirect method is that impurities are detected nonspecifically, or in other words in their totality. As a result, it is possible in a simple way with only a single measurement—or two in the case of the ratiometric variant—to detect impurities. This method is therefore particularly suitable for control and monitoring purposes, in order to trigger suitable procedures in the event of the appearance of impurities. One example of this is quality control in the production of electric lamps, where lamp bulbs with impurities are detected and rejected. By the rapid, simple detection of impurities by measurement techniques, this method can readily be integrated into automated, high-speed production processes.

Virtually all undesired solid impurities—such as residues from the glass forming process—and/or liquid and/or gaseous or vapor-form impurities that can get into the lamp vessel, for instance in the pumping-out or filling process, are detected. In particular, the detectable impurities include the elements of oxygen (O), hydrogen (H), nitrogen (N), carbon (C), silicon (Si), or compounds of these elements, such as water ($H_2O$) or hydrocarbons (CH), and others. The source of these impurities may be leaks or defects in the pumping system (examples being O, $H_2O$, oil vapors) or individual contaminated components (for instance, O from oxidized electrode surfaces, $H_2O$ incorporated into electrode surfaces or hygroscopic metal halides). Silicon can occur as a film on the electrodes, for instance caused by defective pinches of the lamp bulb.

In lamp technology, noble gases are used, such as argon (Ar), krypton (Kr), xenon (Xe) or helium (He). These gases have spectral lines whose excitation energies are correspondingly high (typically greater than 10 eV) and are thus suitable for the method. One further criterion for the suitability of spectral lines is an intensity that is adequately far above the noise. These demands are ideally met by the spectral lines of argon, with the wavelengths $\gamma_1$=738.4 nm, $\gamma_2$=772.4 nm, and $\gamma_3$=811.5 nm. If the gas to be investigated comprises argon or the gas mixture contains argon, then preferably one or more of these spectral lines are used for the method. In an individual case, optionally those spectral lines which are not covered by the lines of other fill components and their compounds are selected. In an especially preferred variant, the detection is performed with the aid of the quotient of the intensities of the argon spectral lines having the wavelengths $\gamma_1$=772.4 nm and $\gamma_2$=738.4 nm.

For the sake of illustrating the relationships, the following table 1 shows some relevant excitation energies for argon and for the impurities of hydrogen (H), nitrogen (N), oxygen (O), carbon (C) and silicon (Si), along with the wavelengths of the associated spectral lines. It can be seen from this that the excitation energies of the impurities are some of them located considerably below those for argon.

TABLE 1

Excitation energies and corresponding wavelengths of the corresponding optical transitions for argon and some possible impurities (quench partners).

| Component | Excitation energy in eV | Wavelength in nm |
|---|---|---|
| Ar | 13.07 | 811.5 |
|    | 13.30 | 738.4 |
| H  | 12.09 | 656.3 |
| N  | 11.76 | 868.3 |
|    | 11.75 | 870.3 |
| O  | 10.74 | 777.2 |
| C  | 9.17  | 833.5 |
|    | 8.85  | 909.4 |
|    | 8.77  | 965.8 |
| Si | 7.60  | 623.7 |
|    | 7.32  | 725.1 |

In the case of molecular impurities, such as water ($H_2O$), OH radicals, hydrocarbons, along with the electronic excitations the loss channels of the rotational and vibrational excitation also occur. The energies required for this are in the meV range or amount to a few eV (less than about 3 eV) and are thus markedly less in each case than the requisite excitation energies for argon.

In a further concrete embodiment of the method, the intensity of one or more spectral lines of the applicable impurity is measured purposefully. The advantage is that with the aid of this direct method the applicable impurity can be detected specifically or in other words identified, and its concentration can be determined by means of a calibration measurement. This makes it easier to find the source of the possible impurity, such as a defective pumping system if hydrocarbon compounds (oil vapors) appear. The disadvantage is that this direct method is relatively complicated and expensive, since the intensity of at least one line (or band) must be measured and evaluated for each possible impurity.

For determining the concentration of the molecules $N_2$, CN, CH or $C_2$, the intensities of the associated molecular bands at the wavelengths of 357.7 nm, 388.34 nm, 388.9 nm and 468.48 nm or 516.5 nm, respectively, are suitable. To eliminate in-phase interference, these measurement values are referred to the intensity of a suitable pressure-independent spectral line. In the presence of argon, for instance, the spectral line having the wavelength 738.4 nm is suitable. Table 2 shows a listing of some typical impurities for discharge lamps. Also listed are the wavelengths suitable for detecting them directly.

TABLE 2

Typical impurities for discharge lamps and wavelengths suitable for their direct detection.

| Impurity | Wavelength in nm |
|---|---|
| H | 656.3 |
| HgH | 421.9 |
| O | 777.2 |
| $N_2$ | 380.5; 357.7; 337.1 |
| CN | 388.4; 419.2 |
| CH | 388.9; 432.4; 431.4 |
| $C_2$ | 516.5; 473.7; 468.48 |
| Si | 302.0; 300.7 |
| Re | 346.0 |
| W | 400.9 |

An expanded two-stage method combines the direct and indirect measuring methods. In the first method stage, it is first ascertained by the indirect measuring method whether any impurity is present at all. Only if that is the case is a qualitative and/or quantitative determination of the individual components of the impurity performed in the second method stage, by means of the direct measuring method.

A further variant of the method is used to assess the quality of discharge lamps, in particular metal halide high-pressure discharge lamps. In this variant, the time-dependent change in intensity of the spectral lines during the startup phase of the lamps is optionally utilized in addition for assessing the electrode quality. To that end, by means of the lamp electrodes, a glow discharge is generated inside the discharge vessel of the lamp. Depending on the properties and condition of the electrode—for instance, surface, geometry, material—this glow discharge first burns at the electrode shaft, for instance, and then migrates toward the electrode tip. The length of time required for it to do so depends on the quality of the electrode and typically fluctuates between a few tenths of a second and a few seconds. It is longer in an oxidized electrode and/or an electrode contaminated by quartz or other deposits, and in the event of an unsuitable electrode geometry. The startup performance is also affected by impurities possibly located in the discharge vessel and an excessively low fill pressure of the ignition gas, such as argon. If the duration of the startup phase and the course of intensity of the spectral lines during the startup phase are within predeterminable tolerance ranges, then the lamp meets the quality requirements. If not, it can be rejected as defective or unacceptable.

In discharge lamps with solid or liquid fill components, the glow discharge is advantageously operated only at low power and/or only briefly, for instance intermittently. This prevents a significant proportion of these fill components from changing to the vapor phase. If they did so, spectral lines of the vapor could in fact be excited that would cover the spectral lines of possibly present impurities and would thus cause incorrect measurements.

In a concrete embodiment of the method for determining the pressure of argon, the intensity of the spectral line having the wavelength $\gamma=763.5$ nm is determined. Over a wide pressure range, in particular in the range between about 0.1 kPa and about 40 kPa, the intensity of this spectral line increases with the pressure. By means of calibration measurements, the pressure is ascertained directly from the intensity. In a ratiometric variant of the method, this intensity is related to the measured pressure-independent intensity of a second spectral line. The spectral line of argon having a wavelength of 738.4 nm is suitable for this purpose, for instance.

A suitable apparatus for performing the method according to the invention comprises a vessel, in which the gas or gas mixture and the impurities possibly contained therein are located; an energy supply unit, which is connected to the vessel via a coupling device and generates the gas discharge, in particular a glow discharge; a spectroscopic measurement device, which measures the intensity or intensities of the spectral line or lines; and an evaluation device, which from the measured values detects a possible impurity or identifies specific impurities and indicates their concentrations and/or ascertains the (partial) pressure of the gas or of the gas components of the gas mixture.

The vessel may for instance be a lamp bulb or a specimen vessel connected to the pumping or gas mixing system of a lamp production line.

A high-frequency generator, for instance, is suitable as the energy supply unit. In that case, the coupling device can comprise either electrodes located inside the discharge vessel, such as the lamp electrodes of a discharge lamp, or external electrodes. In the latter case, electrodes connected to the high-frequency generator are mounted on the outer wall of the vessel. This variant is also known as capacitive high-frequency discharge with dielectric electrodes. It is suitable also in particular for use in electric incandescent lamps, in which alternatively the incandescent coil itself can act as an internal electrode. In that case, all that is additionally needed is one external (dielectric) electrode. The vessel may also be located in the interior of a coil supplied by the high-frequency generator, so that an inductive high-frequency discharge takes place.

The spectral separating device in the simplest case comprises a narrow-band optical (interference) filter—typical resolutions are between about 5 nm and 10 nm—per spectral line to be measured. Alternatively, a spectrometer is suitable that breaks the radiation down into its spectral components by means of dispersive elements—such as prisms or gratings—or in other words generates an optical spectrum. A further advantage is the higher resolution of a spectrometer—typically 1 nm and below. To increase the detection limit, it may be advantageous to mount additional optical elements, such as lenses or mirrors, between the vessel and the spectral separator, which serve to guide and focus the fluorescent radiation toward the spectral separator.

The evaluation device in the simplest case has one or more detector elements, such as photodiodes or a diode line or diode array. The detector elements convert the spectral components of the radiation into voltage signals—corresponding to respective intensity. An indicator unit renders the voltage signals visible in an analog or digital display. Moreover, the voltage signals may also be delivered to an electronic computer, which for instance performs the quotient formation of the ratiometric variant. As a result and using the calibration values, both the concentration of individual impurities and the gas pressure can then be calculated and output. To improve the signal-to-noise ratio and/or reduce the effects of stochastic intensity fluctuations on the outcomes of measurement, it is advantageous to perform a cumulative averaging over a plurality of identical kinds of measurements with the aid of a computer.

To ascertain the calibration values for the spectroscopic quality control in the production of discharge lamps, the following method has proven itself.

In a first step, limit values for parameters are ascertained that act as a measure of the operability and performance of one lamp type, such as metal halide high-pressure discharge lamps. Suitable lamp parameters are for instance the ignition voltage, that is, the voltage required to ignite the discharge; the startup peak voltage, that is, the value of the maximum that the voltage passes through after the lamp is turned on while a stable arc discharge is building up; the reignition peak voltage, that is, the peak value of the alternating voltage applied to the lamp electrodes; and the arc takeover time, that is, the length of time between when the lamp is turned on and when the arc forms. The values of these electric lamp parameters increase with increasing contamination inside the lamp.

In the second step, in corresponding comparison measurements, the values of the electric lamp parameters are correlated with the spectroscopic measurement values. For example, lamps with defined impurities are produced, measured spectroscopically, and associated with the ascertained corresponding lamp parameters. In this way, a set of ranges of values for the spectral intensities or intensity ratios can be produced for every lamp type and for various degrees of contamination. This set is then used as a reference in an actual determination of the contamination of a lamp or a lamp fill. If the actual measured values—or the ratios calculated from them are within the respective tolerance range, the contamination is slight; if not, it is unacceptable, and the applicable lamp is rejected, or production is discontinued in order to correct the source of the contamination.

A major advantage of spectroscopic quality control is the rapidity of the measurements on which it is based. The result is typically available within only a few seconds. In contrast to this, ascertaining the electric lamp parameters in the context of calibration in the spectroscopic method takes up to several minutes (for example, up to six minutes is tolerated as a limit value for the arc takeover time; that is, one might have to wait that long before the applicable lamp is rejected).

The rapidity predestines the method of the invention for use in high-speed lamp production lines. One variant contemplates the integration of the spectroscopic measurement method into the lamp production process as follows. The fundamental concept here is to introduce rapid spectroscopic online controls into the essential production steps. As a result, impurities are possibly already detected in an early phase of the course of production, rather than only in the finished product as has been typical until now. Consequently—especially in high-speed production lines—the rejection rate can be reduced markedly.

Preferably, spectroscopic measurements are performed in the following three production stages:

1. before filling of the discharge vessel of the lamp and before electrode installation, by means of discharge in a specimen vessel connected to the vacuum ring line, in order to monitor the gas system of the production line for impurities;
2. after the insertion of the electrodes into the discharge vessel, by means of specimen discharge inside the discharge vessel, in particular by means of specimen discharge between the lamp electrodes, for checking the electrode system and the inner wall of the discharge vessel for impurities; and
3. after the filling and closure of the discharge vessel, by means of specimen discharge inside the discharge vessel, in particular by means of specimen discharge between the lamp electrodes, to check whether the impurities inside the finished lamp are within a predeterminable tolerance range. If the measured values are within the tolerance range, the applicable discharge vessel or the corresponding complete lamp is released for its intended use; if not, it is rejected.

DRAWINGS

The invention will be described in further detail below in terms of several exemplary embodiments. Shown are.

DETAILED DESCRIPTION

Figure 1:
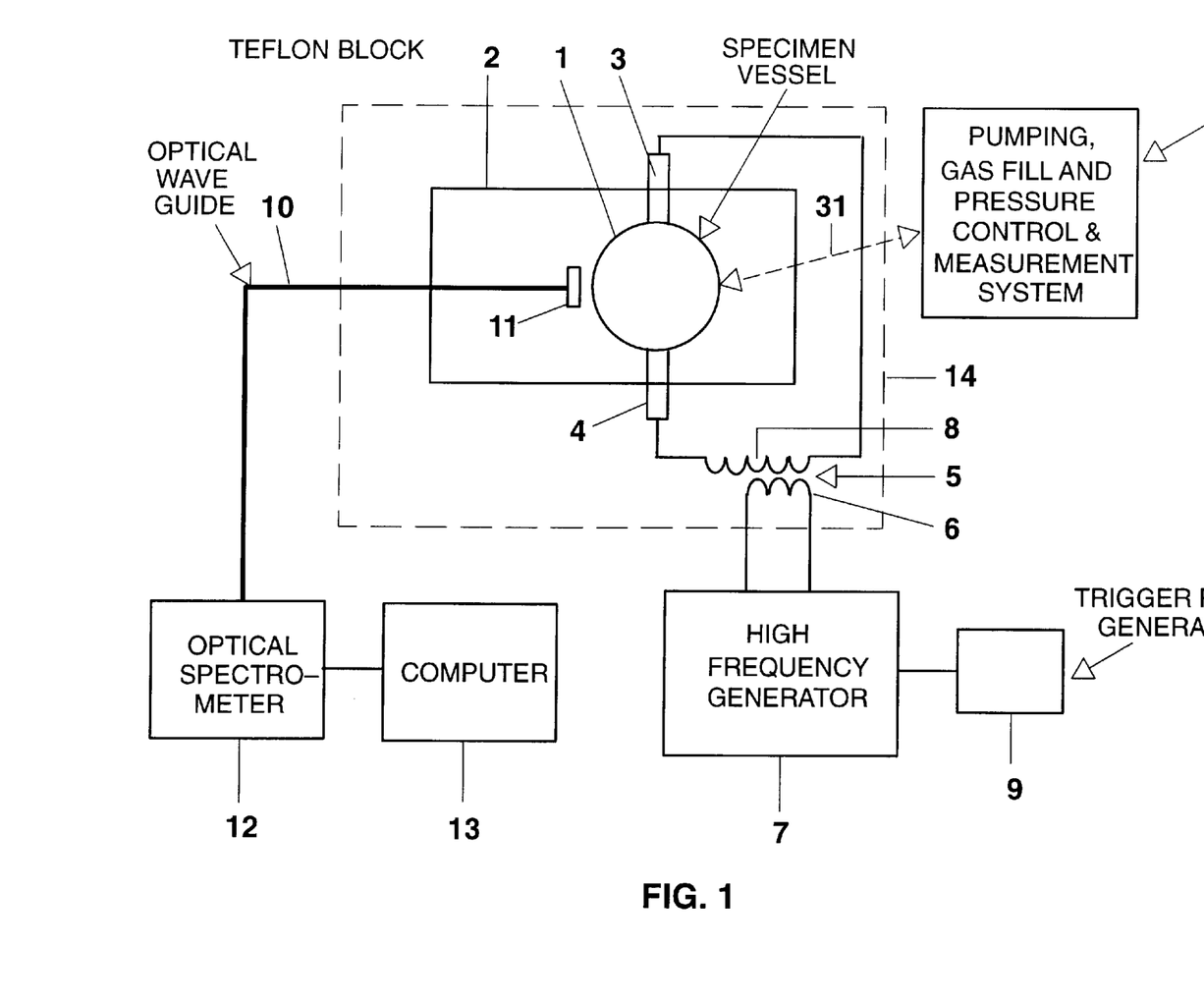
FIG. 1, a schematic illustration of an apparatus for the spectroscopic detection of impurities and for determining the gas pressure in a specimen vessel.

FIG. 1 shows a schematic illustration of an apparatus for performing the method for detecting and determining the concentration of impurities and for determining the gas pressure in a specimen vessel. The apparatus comprises a tubular specimen vessel 1 (shown schematically in cross section) of glass; a solid rectangular block 2 of Teflon® that partly surrounds the specimen vessel 1; two metal pinlike electrodes 3, 4 that protrude partway into the block 2, where they are located diametrically opposite one another on the outer wall of the specimen vessel 1; a high-voltage transformer 5, whose primary winding 6 is connected to a high-frequency generator 7 and whose secondary side 8 is connected to the electrodes 3, 4; a trigger pulse generator 9, which is connected to the high-frequency transmitter 7; an optical waveguide 10, whose first end protrudes into part of the block 2 and is located in the vicinity of the outer wall of the specimen vessel 1; an ordering filter 11 located immediately before the face end of the first end of the optical waveguide 10; an optical spectrometer 12, whose input is connected to the second end of the optical waveguide 10 and whose output is connected to a computer 13; and a metallic shielding housing 14, which surrounds the block 2 with the specimen vessel 1, the electrodes 3, 4, the ordering filter 11 and the high-voltage transformer 5, the optical waveguide 10 and the connecting cable between high-voltage transformer 5 and the high-frequency transmitter 7 being extended through corresponding openings in the shielding housing 14 into its interior.

The diameter of the tubular specimen vessel 1 is approximately 20 mm. It has one metal flange on each of its two face ends (the flange is not shown in the schematic cross-sectional view of the specimen vessel 1). By means of the metal flanges, the previously evacuated specimen vessel 1 is connected during lamp production, typically to a gas filling and pumping system 30 or a gas-filled production cell—also called a "glovebox"—and filled with the working or filling gas or gas mixture. The double arrows at the connecting line 31 indicate that vacuum can be applied, gas introduced, and that the pressure conditions and fill pressures are measured. The gas or gas mixture in the interior of the specimen vessel 1 is ionized with the aid of the electrodes 3, 4, the high-voltage transformer 5 and the high-frequency transmitter 7. To that end, the high-frequency transmitter 7 furnishes an alternating voltage at a frequency of approximately 120 kHz, which by means of the high-voltage transformer 5 attains a peak-to-peak value of up to 49 kV between the electrodes 3, 4. The maximum power coupling into the gas discharge is approximately 200 W. The high-frequency transmitter 7 is triggered by the trigger pulse generator 9. Some of the fluorescent radiation of the gas discharge is fed into the optical waveguide 10 via the ordering filter 11, which transmits only radiation above about 300 nm. This radiation is delivered to the spectrometer 12, which has a focal length of 0.5 m and a grating (not shown) with 100 lines per millimeter. The spectrum generated by the grating is projected onto a diode array (not shown). The individual diodes of the array convert the radiation intensities of narrow wavelength ranges of 0.5 nm in corresponding voltage signals. The voltage signals are carried to the computer 13 for further processing in accordance with the methods of the invention.

Figure 1A:
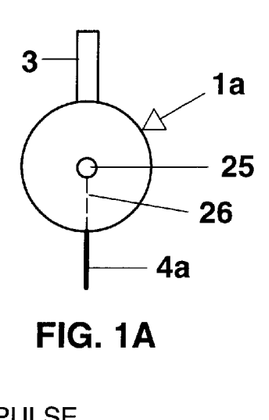
FIG. 1A is a fragmentary schematic illustration of an alternative apparatus for use with an incandescent lamp.

FIG. 1A shows, schematically, an incandescent lamp 1a with an incandescent coil 25 therein, connected by a lamp lead 26 to electrode 4a, corresponding to electrode 4 (FIG. 1), but which need not contact the lamp at the outside as does electrode 4 in FIG. 1. Only one external dielectric electrode 3 is needed.

Figure 2:
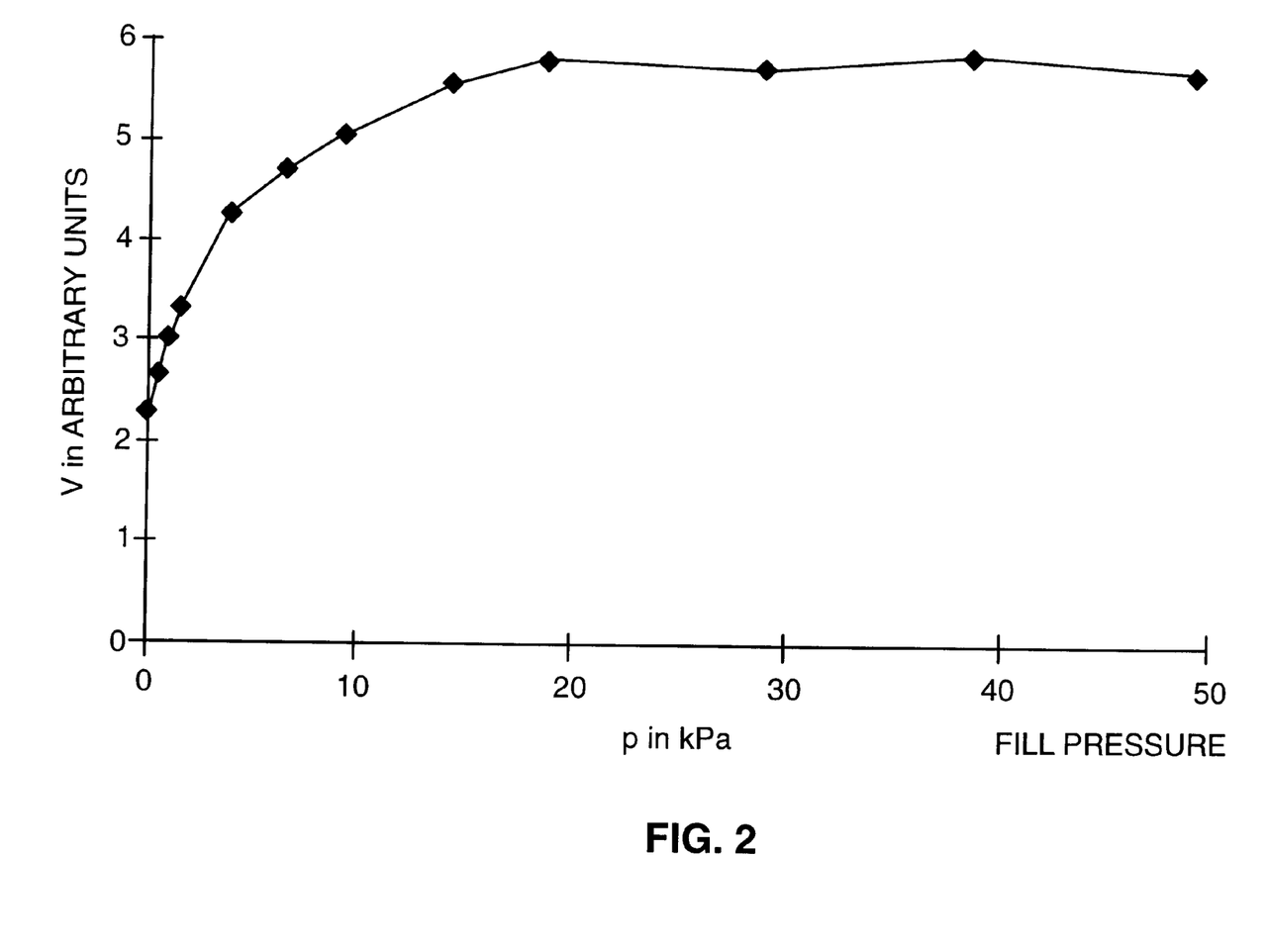
FIG. 2, the ratio, ascertained with the apparatus of FIG. 1, between the intensities of two spectral lines of argon having the wavelengths 763.5 nm and 738.4 nm as a function of the argon fill pressure in the specimen vessel 1.

FIG. 2 shows as an example the measurement outcomes, attained with the apparatus of FIG. 1, for various argon fill pressures. It shows the ratio V of the intensities of two spectral lines of argon, having the wavelengths 763.5 nm and 738.4 nm, in arbitrary units as a function of the argon fill pressure p in kPa in the specimen vessel 1 of FIG. 1. As can be seen from FIG. 2, the ratio increases initially steadily with the pressure. Beyond a pressure of approximately 20 kPa, the ratio remains substantially constant over a wide pressure range. The reason for this is the electrode voltage limited to 49 kV. As comparison measurements with a piezoresistive manometer show, the pressure can be determined with the apparatus of FIG. 1 and the method described with an accuracy of 5% up to an argon fill pressure of approximately 20 kPa.

Figure 3:
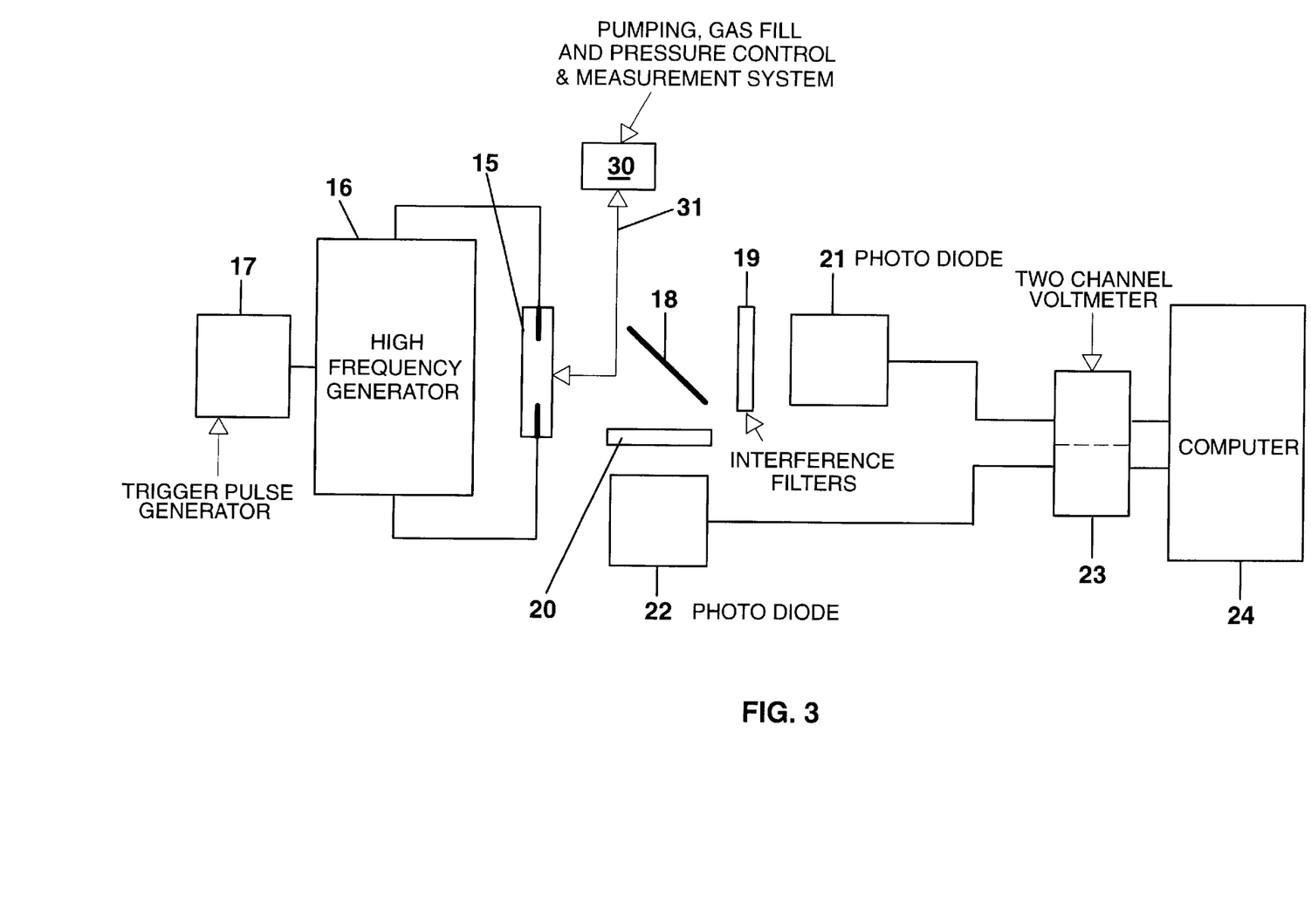
FIG. 3, a schematic illustration of an apparatus of the spectroscopic detection of impurities inside the discharge vessel of a lamp.

FIG. 3 schematically shows an apparatus for performing the method for detecting impurities inside the discharge vessel of a lamp. The apparatus comprises a metal halide high-pressure discharge lamp 15; a high-frequency generator 16 that is connected to the electrodes of the lamp 15 and triggered by a trigger pulse generator 17; a semitransparent mirror 18; two interference filters 19, 20, each with a photodiode 21, 22 following it—the first interference filter 19 including the associated photodiode 21 facing the transmitting side of the mirror 18 and the second interference filter 20 including the associated photodiode 22 facing the reflective side; a two-channel volt meter 23 connected to the photodiodes 21, 22; and a computer 24, which is connected to the two channels of the volt meter 23.

With the aid of the high-frequency transmitter 16, a low-power glow discharge, typically from a few tenths of a watt to several watts, is ignited for a brief period of time, typically a few tenths of a second to several seconds. As a result, on the one hand the ignition gas, argon, and the possibly present impurities inside the lamp 15 are excited to fluorescence; on the other, however, a significant excitation of the remaining fill components of the lamp is prevented. The interference filters 19 and 20 are transparent only for radiation in a range of ±2 nm around the wavelength of about 738.5 nm or 772.4 nm. The photodiodes 21, 22 generate voltage signals, each corresponding to the intensity of the spectral radiation components, and these signals are measured by the two channels of the volt meter 23. The computer 24 reads off the two channels, calculates the ratio of the corresponding voltage values, and from that and by means of a calibration value ascertains a figure of merit. If the figure of merit is within a tolerance range, the lamp 15 meets the quality requirements. If not, it is rejected as defective on the basis of unacceptable impurities.

The invention is not limited to the exemplary embodiments described. In particular, individual characteristics of various exemplary embodiments may also be combined with one another.

We claim:

1. A method for detecting impurities in gases, especially noble gases, or gas mixtures for at least one electric lamp or lamps or radiators, comprising the steps of exciting, by means of a gas discharge, the gas or gas components of the gas mixture and the impurities possibly contained in the lamps, or said gas or gas mixture to emit electromagnetic radiation extending over a radiation spectrum;

and comprising, in accordance with the invention, the steps of determining any possibly present impurities in said gases or gas mixtures by selecting, within a spectral portion of said radiation spectrum, at least one spectral line having an intensity which is largely independent of pressure in the relevant region of pressures of gases or gas mixtures, for said electric lamp or lamps or radiators, and measuring the intensity of the so selected spectral line or lines and thereby determining any possibly present impurities.

2. The method of claim 1, wherein said selection step comprises selecting the spectral line or lines of the gas or gas components whose wavelength or wavelengths correspond to a higher excitation energy than that of the impurities expected to be detected.

3. The method of claim 2, wherein the gas or gas mixture comprises argon, and said selecting step comprises selecting one or more of the spectral lines of argon having the wavelengths of 738.4 nm, 772.4 nm, 811.5 nm.

4. The method of claim 1, wherein said selection step comprises selecting a spectral line of an expected impurity; and wherein said measuring step comprises measuring the intensity of said spectral line as a measure for the concentration of the impurity.

5. The method of claim 1, wherein said possible impurities comprise at least one of the molecules $N_2$, CN, CH or $C_2$, or a combination of said molecules.

6. The method of claim 4, wherein the wavelengths of said expected impurities are 357.7 nm, 388.34 nm, 388.9 nm and 468.48 nm or 516.5 nm, and wherein each of said wavelengths is a spectral fragment of a molecular band of the molecules of at least one of said impurities.

7. The method of claim 4, wherein said gas or gas mixture comprises or contains argon; and the spectral intensity of the expected impurity is standardized to the intensity of argon in a pressure region in which the spectral intensity of argon is largely independent of pressure.

8. The method of claim 7, wherein the wavelength of the argon spectral line is 738.4 nm.

9. The method of claim 1, wherein said selection step comprises selecting two spectral lines which are close together, and said measuring step comprises forming a quotient of the intensity of said two closely adjacent spectral lines, so that noise signals and in-phase interference signals are largely eliminated by the adjacent position of said spectral lines in the course of the formation of the quotient.

10. The method of claim 9, wherein said two spectral lines are so spaced that the difference in wavelength is less than about 100 nm.

11. The method of claim 10, wherein the difference in wavelengths of the two spectral lines is less than about 50 nm.

12. The method of claim 9, wherein said selection step comprises selecting spectral lines with wavelengths in the range of between 650 nm and 1000 nm to form said quotient.

13. The method of claim 11, wherein said gas or gas mixture comprises or contains argon, and wherein said selection step comprises selecting the spectral lines of the argon having the wavelengths of $\lambda_1$=772.4 nm and $\lambda_2$=738.4 nm, from which spectral lines the quotient of the intensities is formed.

14. The method of claim 1, wherein said step of exciting the gas mixture comprises exciting the gas mixture to generate to the extent of generating a glow discharge within the respective electric lamp or radiator.

15. The method of claim 1, wherein said step of exciting the gas or gas components by means of a gas discharge comprises generating electromagnetic energy of high frequency and applying said so generated high-frequency energy to said gas or gas components.

16. The method of claim 1, wherein said step of exciting the gas or components by means of a gas discharge comprises generating a gas discharge within the interior of a high-pressure discharge lamp;

measuring the duration until said at least one spectral line has reached a quasi-steady state value after a start-up phase of the lamp; and ascertaining at least one impurity of the gas or gas mixture within the lamp and forming the lamp fill, and electrode quality as a function of the magnitude of the intensity of said at least one spectral line, and, optionally, further the duration until the intensity of said at least one spectral line has reached a quasi-steady state value after the start-up phase of the lamp.

17. The method of claim 1, wherein said gas or gas mixture and forming a lamp fill are retained within the interior of a discharge lamp, and said gas or gas mixture is excited to form a gas discharge therein; and further including the following steps:
a) ascertaining electrical parameters of the lamp that are characteristic for the operability and performance of said lamp;
b) then carrying out said selecting and measuring steps by measuring said intensity of said at least one spectral line and ascertaining electrical parameters of the lamp by repeating said ascertaining steps and spectral line measuring steps for variously impurity contaminated lamps, optionally including lamps that, due to impurities, have poor ignition or are incapable of igniting or forming a stable arc discharge or, if so, only with out-of-design parameter delay; and
c) associating the electrical values to corresponding spectroscopic values, to obtain a set of calibrated reference values of spectral intensities, or intensity ratios, to permit spectroscopic assessment of the quality of lamps having said ascertained electrical parameters.

18. A method for determining the pressure of gases, especially noble gases, and forming a fill for electric lamps or radiators, or of gas components or gas mixtures for said fill, comprising the steps of exciting, by means of a gas discharge, the gas or gas components of the gas mixtures, and of impurities possibly contained in the lamps or said gas or gas mixture to emit electromagnetic radiation extending over a radiation spectrum, and comprising, in accordance with the invention, the steps of determining the magnitude of the pressure or partial pressure of said fill by selecting, within a spectral portion of said radiation spectrum, at least one spectral line having an intensity which is largely dependent upon pressure of said gases or gas mixtures for said electric lamps or radiators; and measuring the intensity or intensities of said at least one so selected spectral line or lines, to thereby determine the pressure or partial pressure of the gas or the corresponding gas component.

19. The method of claim 18, wherein the gas or gas mixture comprises argon, and said selecting step comprises selecting the spectral line having the wavelength γ=763.5 nm.

20. The method of claim 18, wherein said selection step comprises selecting two spectral lines which are close together, and said measuring step comprises forming a quotient of the intensity of said two closely adjacent spectral lines, so that noise signals and in-phase interference signals are largely eliminated by the adjacent position of said spectral lines in the course of the formation of the quotient.

21. The method of claim 20, wherein the difference in the wavelengths of the two spectral lines is less than about 100 nm.

22. The method of claim 21, wherein the difference is less than 50 nm.

23. The method of claim 20, wherein the gas or gas mixture comprises argon, and said selection step comprises selecting the spectral line of the argon having the wavelength 738.4 nm, said wavelength being used to form said quotient.

24. The method of claim 18, wherein said step of exciting the gas mixture comprises exciting the gas mixture to generate to the extent of generating a glow discharge within the respective electric lamp or radiator.

25. The method of claim 18, wherein said step of exciting the gas or gas components by means of a gas discharge comprises generating electromagnetic energy of high frequency and applying said so generated high-frequency energy to said gas or gas components.

26. A method for spectroscopically detecting impurities in gases, especially noble gases, or gas mixtures, for electric lamps or radiators, and forming a fill for said lamps or radiators, said method being integrated into the production process in a production line for discharge lamps, comprising the steps of:
a) before a discharge vessel of a discharge lamp is filled, spectroscopically measuring, by means of a specimen discharge inside the gas system of the lamp production line, said fill to monitor the gas system of the production line for impurities;
b) inserting electrodes into the discharge vessel, and then spectroscopically measuring, by means of a specimen discharge inside the discharge vessel and after the insertion of the electrodes therein to, the spectral lines emitted from a discharge, to thereby monitor the electrode system and the wall of the discharge vessel for impurities;
c) filling and closing the discharge vessel and then spectroscopically measuring, by means of a specimen discharge inside the discharge vessel, to check whether the impurities in the interior of the finished lamp are within a predetermined tolerance range; and
wherein said spectroscopic measurement comprises carrying out the steps of
d-1) determining any possibly present impurities in said gases or gas mixtures by
selecting, within a spectral portion of said radiation spectrum, at least one spectral line having an intensity which is largely independent of pressure in the relevant region of pressures of gases or gas mixtures, for said electric lamp or lamps or radiators, and
measuring the intensity of the so selected spectral line or lines and thereby determining any possibly present impurities; or
d-2) determining the magnitude of the pressure or partial pressure of said fill by
selecting, within a spectral portion of said radiation spectrum, at least one spectral line having an intensity which is largely dependent upon pressure of said gases or gas mixtures for said electric lamps or radiators; and
measuring the intensity or intensities of said at least one so selected spectral line or lines, to thereby determine the pressure or partial pressure of the gas or the corresponding gas component.

27. The method of claim 26, further comprising the following additional method step
e) spectroscopically measuring the pressure of the fill inside the vessel as set forth in step d-2) by means of specimen discharge inside the discharge vessel after the filling and closure of the discharge vessel; and
determining whether the cold fill pressure in the interior of the discharge vessel of the finished lamp is within a predetermined tolerance range.

28. The method of claim 26, comprising the following additional method step
f) interrupting production, before the discharge vessel is filled and closed, if the measured values determined by at least one of the method steps a) and b) are outside a predeterminable tolerance range.

29. The method of claim 26, comprising the following additional method step
g) rejecting an affected discharge vessel if the measurement values determined by at least one of method steps c) and d) are outside a predeterminable tolerance range.

30. The method of claim 26, comprising performing the specimen discharge of method step a) in a specimen vessel connected to a vacuum ring line.

31. The method of claim 26, comprising performing the specimen discharges of method steps b) and c) between the electrodes of the specimen discharge vessel.

32. An electric lamp or radiator test apparatus carrying out a method of detection of impurities in a lamp fill formed of gases, or gas mixtures, or of fill pressure, in which any possibly present impurities in said gases or gas mixtures are determined by selecting, within a spectral portion of said radiation spectrum, at least one spectral line having an intensity which is largely independent of pressure in the relevant region of pressures of gases or gas mixtures, for said electric lamp or lamps or radiators, and measuring the intensity of the so selected spectral line or lines and thereby determining any possibly present impurities; or the magnitude of the pressure or partial pressure of said fill is determined by selecting, within a spectral portion of said radiation spectrum, at least one spectral line having an intensity which is largely dependent upon pressure of said gases or gas mixtures for said electric lamps or radiators; and measuring the intensity or intensities of said at least one so selected spectral line or lines, to thereby determine the pressure or partial pressure of the gas or the corresponding gas component;

said apparatus comprising
a vessel (1; 15), in which the gas or gas mixture and the impurities possibly contained therein are located;
an energy supply unit (7, 16), which is connected to the vessel (1) via a coupling device (3, 4, 5) and generates the gas discharge;
a spectroscopic measurement device (12; 18–22), which measures the intensity or intensities of said spectral line or lines generated by said discharge;

an evaluation device (13; 23, 24) coupled to the spectroscopic measuring device (12, 18–22), which from the measured values ascertains the concentration of the impurities or the pressure or partial pressure of the gas or gas component by selecting, respectively, at least one spectral line which is pressure-independent or, respectively, a plurality of spectral lines independent of pressure, and measuring the intensity or intensities of the selected spectral line or lines; and a pumping, gas fill, and pressure control and measuring system (30) coupled to said lamp, lamps, radiators and providing said fill, under controlled pressure.

33. The apparatus of claim 32, wherein the energy supply unit comprises a high-frequency generator (7; 16), the coupling device comprises a high-voltage transformer (5) and two high-frequency (HF) electrodes (3, 4), the HF electrodes being connected to the secondary winding (8) of the transformer (5); and the high-frequency generator (7) being connected to the primary winding (6) of the high-voltage transformer (5).

34. The apparatus of claim 32, wherein the vessel comprises a discharge vessel of a discharge lamp (15), two lamp electrodes being located in the interior of the discharge vessel, each being connected to power supply leads extending to the outside in gastight manner and in turn being connected to the energy supply unit (16), so that the lamp electrodes are a component of the coupling device.

35. The apparatus of claim 33, wherein at least one of the HF electrodes (3, 4) is located on the outer wall of the vessel.

36. The apparatus of claim 35, wherein the vessel comprises the lamp bulb of an incandescent lamp, on the outer wall of which a first HF electrode is mounted, an incandescent coil (25) being located in the interior of the bulb, the coil being coupled to the high-frequency generator (7), so that the incandescent coil acts as a second HF electrode.

37. The apparatus of claim 32, wherein the spectroscopic measurement device comprises a spectrometer (12), the radiation being spectroscopically analyzed in regard to its spectral components and providing an analysis output corresponding to their respective intensity.

38. The apparatus of claim 37, wherein the evaluation device (3; 23, 24) comprises a computer, which receives and reads the analysis output and processes and said output and, as a result, outputs the value of at least one of the gas pressure, and the concentration of the impurity or impurities.

* * * * *